US006380222B2

(12) United States Patent
Lindberg et al.

(10) Patent No.: US 6,380,222 B2
(45) Date of Patent: Apr. 30, 2002

(54) USE OF AN H+, K+-ATPASE INHIBITOR IN THE TREATMENT OF NASAL POLYPS

(75) Inventors: Per Lindberg, Mölndal (SE); Joan Piñas-Massó, Barcelona; Jordi Serra-Carreras, Manresa, both of (ES); Jan Trofast, Lund (SE)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 09/833,699

(22) Filed: Apr. 13, 2001

Related U.S. Application Data

(62) Division of application No. 09/043,278, filed as application No. PCT/SE97/01651 on Oct. 1, 1997, now abandoned.

(30) Foreign Application Priority Data

Oct. 11, 1996 (SE) ............................................. 9603725

(51) Int. Cl.[7] ........................ A61K 31/41; A61K 31/415
(52) U.S. Cl. ........................................ 514/339; 514/395
(58) Field of Search .................................. 514/339, 395

(56) References Cited

U.S. PATENT DOCUMENTS

| 4,199,578 A | 4/1980 | Stevenson | ................... 424/240 |
|---|---|---|---|
| 4,364,923 A | 12/1982 | Cook et al. | ................... 424/46 |
| 4,758,579 A | 7/1988 | Kohl et al. | ................. 514/338 |

FOREIGN PATENT DOCUMENTS

| EP | 0005129 | 10/1979 |
|---|---|---|
| EP | 0174726 | 3/1986 |
| GB | 2163747 | 3/1986 |
| WO | 9703659 | 2/1997 |

OTHER PUBLICATIONS

VJ Lund Diagnosis and treatment of nasal plyps Brit. Med. J. 1995, 311, 1411–14.

J. Clin. Gastroenterol, vol. 23, No. 1, 1996, p. 53–54.

American Journal of Gastroenterology, vol. 91, No. 10, 1996, p. 2245–2246.

*Primary Examiner*—Zohreh Fay
(74) *Attorney, Agent, or Firm*—White & Case LLP

(57) ABSTRACT

The invention provides a method for the treatment of polyposis which comprises treating a subject suffering from polyposis with an $H^+,K^+$-ATPase inhibitor and, optionally, a glucocorticoid. The invention also relates to a pharmaceutical formulation for simultaneous, separate or sequential administration in the treatment of Widal's Syndrome and in the treatment of asthma.

8 Claims, No Drawings

USE OF AN H+, K+-ATPASE INHIBITOR IN THE TREATMENT OF NASAL POLYPS

This application is a divisional of U.S. application Ser. No. 09/043,278, filed Mar. 13, 1998 now abandoned, which is a 371 of International Application No. PCT/SE97/01651, filed Oct. 1, 1997.

FIELD OF THE INVENTION

The present invention provides a new treatment for polyposis using proton pump inhibitors (PPIs), i.e. $H^+,K^+$-ATPase inhibitors.

BACKGROUND OF THE INVENTION

Polyposis can generally arise in the nose and the gastrointestinal tract. In the nose, polyps are pale bags of tissue that arise in the nasal cavity. Their paleness is generally due to poor blood supply. It is not known what causes the polyps to be formed but their presence is often associated with certain medical conditions, for example asthma and aspirin intolerance. Within the general population the incidence of nasal polyps is low at around only 1% but 13% of asthma sufferers and 36% of aspirin intolerant asthmatics suffer from nasal polyposis. The triple condition of nasal polyposis, aspirin intolerance and asthma is known as Widal's Syndrome.

Nasal polyposis is generally treated in two stages. Initially a reduction in size of the polyps is achieved either by surgery or by the application of a topical intranasal steroid preparation, for example betamethasone sodium phosphate. Once a reduction in size has been obtained then long term maintenance of the reduction is necessary by regular use of an intranasal steroid spray such as beclomethasone dipropionate, budesonide, or fluticasone propionate. When rapid amelioration is required, oral steroids such as prednisolone or dexamethasone or synthetic adrenocorticotrophic hormones are used (see V J Lund Diagnosis and treatment of nasal polyps Brit Med J 1995, 311, 1411-4). There are also proposals that non-steroidal antiinflammatory drug can be used in the treatment of nasal polyposis (see WO 9703659-A).

DETAILED DESCRIPTION OF THE INVENTION

According to the invention there is provided a method for the treatment of nasal polyps which method comprises treating a subject suffering from the said condition with an $H^+$, $K^+$-ATPase inhibitor. The invention further provides the use of an $H^+,K^+$-ATPase inhibitor in the manufacture of a medicament for the treatment of nasal polyps.

$H^+,K^+$-ATPase inhibitors are a known class of pharmaceutical agents generally used in therapy for the treatment of gastric acid related diseases. Examples of $H^+,K^+$-ATPase inhibitors are for instance compounds known under the generic names omeprazole, lansoprazole, pantoprazole, rabeprazole and leminoprazole. Some of these compounds are for instance disclosed in EP-A1-0005129, EP-A1-174726, EP-A1-166287 and GB 2163747.

These pharmaceutical substances are generally known to be useful for inhibiting gastric acid secretion in mammals and man by controlling gastric acid secretion at the final step of the acid secretory pathway. Thus, in a more general sense, they may be used for prevention and treatment of gastric-acid related diseases in mammals and man, including e.g. reflux oesophagitis, gastritis, duodenitis, gastric ulcers and duodenal ulcers.

It has now surprisingly been found that $H^+,K^+$-ATPase inhibitors are useful in the treatment of nasal polyps, particularly where known treatments have failed.

The $H^{30},K^+$-ATPase inhibitors preferably used in the invention are compounds of the general formula (I)

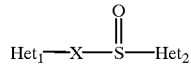

wherein $Het_1$ is

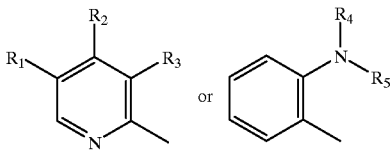

$Het_2$ is

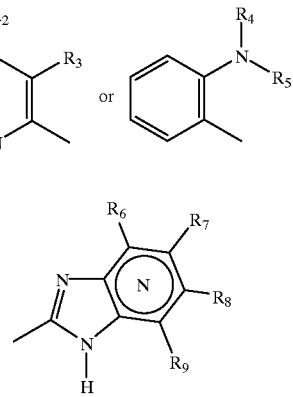

and X is

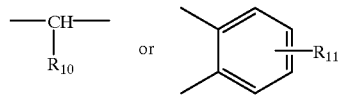

wherein N in the benzimidazole moiety of $Het_2$ means that one of the ring carbon atoms substituted by $R_6$–$R_9$ optionally may be exchanged for a nitrogen atom without any substituents;

$R_1$ and $R_3$ each independently represent hydrogen, alkyl, or alkoxy on the condition that $R_1$ and $R_3$ do not simultaneously represent alkoxy; and $R_2$ represents alkyl, alkoxy optionally substituted by fluorine, alkylthio or alkoxyalkoxy; or one of $R_1$ and $R_3$ is halogen and the other is hydrogen and $R_2$ is 1-morpholino, 1-piperidino or dialkylamino;

$R_4$ and $R_5$ are the same or different and selected from hydrogen and alkyl;

$R_6$–$R_9$ are the same or different and selected from hydrogen, halogen, alkyl, alkoxy, haloalkoxy, alkylcarbonyl, and alkoxycarbonyl;

$R_{10}$ is hydrogen or $R_{10}$ and $R_3$ together complete a ring containing 6 to 8 carbon atoms; and $R_{11}$ represents hydrogen, halogen or alkyl;

wherein the compound of formula (I) is optionally in the form of an pharmaceutically acceptable alkaline salt or in its neutral form or is a single enantiomer or a racemic mixture thereof;

wherein each alkyl or alkylenyl moiety has a branched or straight chain and has 1 to 6, preferably 1 to 4, carbon atoms;

wherein a halogen atom is preferably a fluorine, chlorine, or bromine atom, preferably a fluorine or chlorine atom.

Examples of particularly preferred compounds according to formula I for use in the invention are

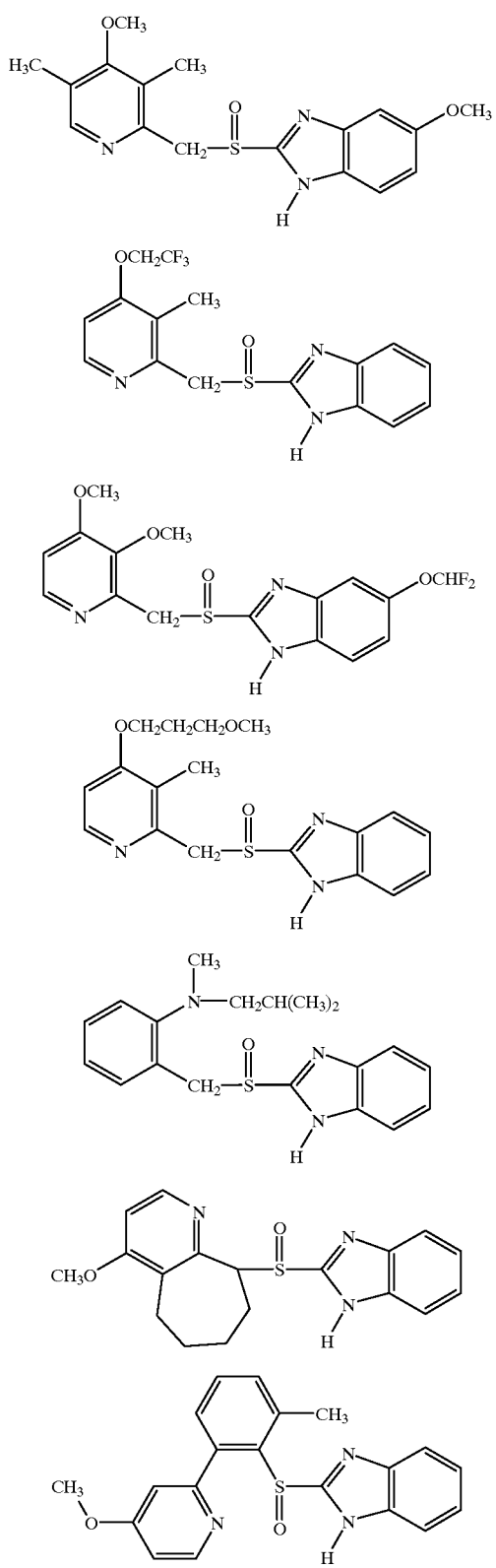
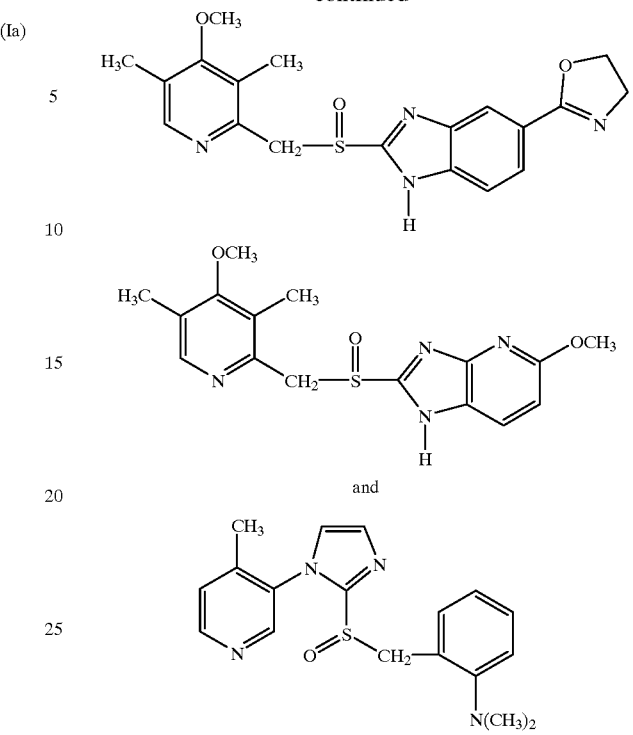

The $H^+,K^+$-ATPase inhibitor used in the invention is preferably of formula (Ia): in other words it is preferably omeprazole, or an alkaline salt of omeprazole, the (−)-enantiomer of omeprazole or an alkaline salt thereof.

The compound of formula (I) when optionally in the form of a pharmaceutically acceptable alkaline salt is preferably the $Mg^{2+}$, $Ca^{2+}$, $Na^+$ or $K^+$ salt, more preferably the $Mg^{2+}$ salt.

The $H^{30}$, $K^+$-ATPase inhibitor used in the invention can be administered orally, rectally or parenterally. While the effect of the inhibitors on the nasal polyps has been established in patients who have taken omeprazole by the oral route, it is believed that the effect of the inhibitor on the polyps is a systemic effect that is not dependent on what mode of administration is used. Accordingly a reduction in size of the polyps should be obtainable with other routes of administration.

Commercially available pharmaceutical preparations of $H^{30}$, $K^+$-ATPase inhibitors are suitably used in the invention. Examples of such preparations for omeprazole include enteric coated pellets of omeprazole filled in capsules, or formulated into a multiple unit tabled dosage form; enteric coated tablets of omeprazole or an alkaline salt thereof; and solutions for parenteral administration comprising an alkaline salt of omeprazole.

The dose of the $H^+,K^+$-ATPase inhibitor to be administered will vary according to the type of nasal polyps to be treated and the condition of the patient. However the dosage for oral, rectal or i.v. administration is generally in the range of from 1 to 100 mg of $H^+,K^+$-ATPase inhibitor per day. Normally an amount of from 10 to 40 mg per day is used for oral administration.

The invention may be applied in combination with other treatments known to ameliorate the other symptoms generally associated with nasal polyps, for example asthma. In other words, the invention can be applied in the treatment of Widal's Syndrome which consists of the conditions of nasal polyps, asthma and aspirin intolerance. The invention may also be applied in the treatment of other inflammatory diseases in the upper respiratory tract such as acute and chronic rhinosinusitis, allergic and non-allergic rhinitis, as well as in the lower respiratory tract such as asthma. Therefore according to the invention there is further provided a method for treating Widal's Syndrome and other respiratory tract inflammatory diseases which method comprises simultaneously, separately or sequentially administration to a subject suffering from the syndrome or the diseases a pharmaceutical formulation comprising an $H^+,K^+$-ATPase inhibitor and a glucocorticoid. According to the invention there is also provided a pharmaceutical formulation for simultaneous, separate or sequential administration to be used in the treatment of Widal's Syndrome or in the treatment of asthma which formulation comprises an $H^+,K^+$-ATPase inhibitor and a glucocorticoid. The invention further provides the use of an $H^{30}$, $K^+$-ATPase inhibitor and a glucocorticoid in the manufacture of such a pharmaceutical formulation.

Preferred glucocorticoids are topically active anti-inflammatory steroids. Examples of suitable steroids include budesonide; rofleponide; rofleponide palmitate; ciclesonide; mometasone furoate; fluticasone propionate; 16α, 17α-butylidenedioxy-6α, 9α-difluoro-11β, 21-dihydroxypregna-1,4-diene-3,20-dione; 6α, 9α-difluoro-11β-hydroxy-16α, 17α-dibutylidenedioxy-17α-methylthio-androsta-4-ene-3-one; S-methyl-16α, 17 α-butylidenedioxy-6α, 9α-difluoro-11β-hydroxy-3-oxo-androsta-1,4-diene 17β-carbothioate; methyl 9α-chloro-6α-fluoro-11α-hydroxy-16α-methyl-3-oxo-17α-propionyloxy-androsta-1,4-diene-17α-carboxylate; 6α,9α-difluoro-11β-hydroxy-16α-methyl-3-oxo-17α-propionyloxy-androsta-1,4-diene-17β-carbothioic acid S-(2-oxo-tetrahydro-furan-3S-yl) ester; tipredane; fluocinolone acetonide; flunisolide; flumethasone; dexamethasone; betamethasone; beclomethasone dipropionate; deflazacort; cortivazol; or cortisol and/or hydrocortisol, optionally in their pure isomeric forms (where such forms exist) and in the forms of their pharmaceutically acceptable salts.

The steroids for use in the invention may be applied using conventional dosing rates, e.g. 40 to 3000 μg per day. Administration may be by inhalation orally or intranasally. The steroids can optionally be adapted to be administered from a dry powder inhaler, a pressurised metered dose inhaler, or a nebuliser.

When the steroids are administered from a pressurised inhaler, they are preferably in micronised form. They are suspended or dissolved in a liquid propellant mixture. The propellants which can be used include chlorofluorocarbons, hydrocarbons or hydrofluoroalkanes. Especially preferred propellants are P134a (tetrafluoroethane) and P227 (heptafluoropropane) each of which may be used alone or in combination. They are optionally used in combination with other propellants and/or surfactants and/or other excipients, for example ethanol, surfactants, lubricants, anti-oxidants and stabilising agents.

When the steroids are administered via a nebuliser they may be in the form of a nebulised aqueous suspension or solution, with or without a suitable pH or tonicity adjustment, either as a unit dose or multidose device.

The invention is described more in detail with reference to the following examples.

EXAMPLE 1

A 53 year old woman who had had Widal's Syndrome for several years but who had refused surgical treatment of her polyps suffered mild upper abdominal pain and no improvement in the polyps after treatment by topical and systemic corticosteroids. However within two weeks of being prescribed 20 mg of omeprazole per day in addition to 100 μg of budesonide (Aqua preparation) per nostril/b.i.d. and 6 mg of deflazacort per day, she experienced a progressive improvement in her nasal respiratory problem. Eventually she recovered completely from the polyps.

EXAMPLES 2 TO 10

Nine patients, each with the conditions shown in the following Table 1, were treated during a two week period. The treatment consisted of 20 mg of omeprazole, 100 μg of intranasal budesonide and 3 to 15 mg of oral deflazacort (deflazacort was used in such a small quantity to ensure the patients' compliance). The results are also shown in Table 1.

TABLE 1

| Example No. | Condition | Result |
| --- | --- | --- |
| 2 | Widal's Syndrome | Temporary benefit |
| 3 | Widal's Syndrome | Positive effect |
| 4 | Widal's Syndrome | Positive effect |
| 5 | Nasal Polyposis | Long term benefit |
| 6 | Nasal Polyposts | No benefit |
| 7 | Nasal Polyposis | Positive effect |
| 8 | Nasal Polyposis | Positive effect |
| 9 | Nasal Polyposis and aspirin intolerance | Positive effect |
| 10 | Nasal Polyposis and asthma | No benefit |

Where a positive effect is indicated, this means that the patient experienced a decrease in rhinorrhoea, a marked improvement in nasal respiratory ventilation and a reduction in the size of the polyps. The patient who experienced a temporary benefit by the treatment suffered a recurrence of the polyposis following the withdrawal of omeprazole and deflazacort (topical anti-inflammatory steroids, i.e. budesonide, were taken as required). However after treatment with the same regimen was resumed, a marked reduction in the size of the polyps was achieved.

The patient of Example 5 who experienced a long term benefit initially experienced no benefit at the end of the initial 2 week treatment period but continued with omeprazole and was rewarded with a positive effect at the end of 2 months.

What is claimed is:

1. A method for the treatment of nasal polyps which comprises administering a pharmaceutical formulation comprising an $H^+$, $K^+$-ATPase inhibitor to a subject in need of such treatment.

2. A method for the treatment of nasal polyps which comprises administering simultaneously, separately or sequentially a pharmaceutical formulation comprising an $H^+,K^+$-ATPase inhibitor and a glucocorticoid to a subject in need of such treatment.

3. The method according to claim 2, wherein the glucocorticoid is a topically active anti-inflammatory steroid.

4. The method according to any one of claims 1, 2 and 3, wherein the $H^{30}$, $K^+$-ATPase inhibitor is a compound of the formula

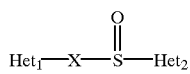

wherein Het₁ is

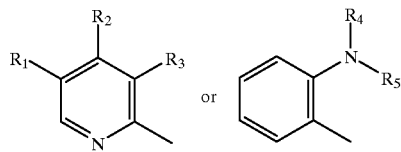

Het₂ is

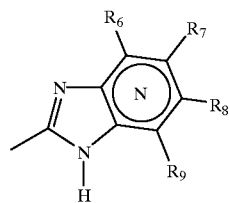

and X=

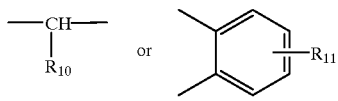

wherein N in the benzimidazole moiety of Het₂ means that one of the ring carbon atoms substituted by $R_6$–$R_9$ optionally may be exchanged for a nitrogen atom without any substituents; $R_1$ and $R_3$ each independently represent hydrogen, alkyl or alkoxy on the condition that $R_1$ and $R_3$ do not simultaneously represent alkoxy; and $R_2$ represents alkyl, alkoxy, fluoro-substituted alkoxy, alkylthio or alkyoxyalkoxy; or one of $R_1$ and $R_3$ is halogen and the other is hydrogen and $R_2$ is 1-morpholino, 1-piperidino or dialkylamino;

$R_4$ and $R_5$ are the same or different and selected from the group consisting of hydrogen and alkyl;

$R_6$–$R_9$ are the same or different and selected from the gorup consisting of hydrogen, halogen, alkyl, alkoxy, haloalkoxy, alkylcarbonyl and alkoxycarbonyl;

$R_{10}$ is hydrogen or R10 and R3 together complete a ring containing 6 to 8 carbon atoms; and $R_{11}$ represents hydrogen, halogen or alkyl;

wherein each alkyl or alkylenyl moiety has a branched or straight chain and has 1 to 6 carbon atoms.

5. The method according to claim 3, wherein the glucocorticoid is budesonide, beclomethasone diproprionate or fluticasone propionate.

6. The method according to claim 4, wherein the compound of formula (I) is in its neutral form or in the form of a pharmaceutically acceptable salt, a single enantiomer or a racemic mixture.

7. The method according to claim 4, wherein the compound of formula (I) is a compound of formula (Ia)

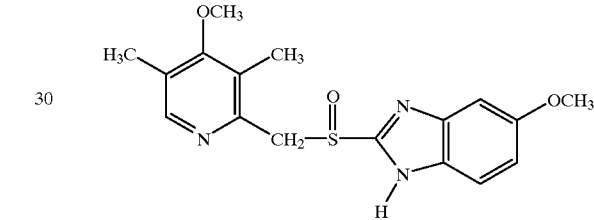

8. The method according to claim 7, wherein the compound of the formula (Ia) is in the form of an alkaline salt, the (−)-enantiomer or an alkaline salt of the (−)-enantiomer.

* * * * *